United States Patent
Chan et al.

(10) Patent No.: US 10,687,757 B2
(45) Date of Patent: Jun. 23, 2020

(54) PSYCHOLOGICAL ACUTE STRESS MEASUREMENT USING A WIRELESS SENSOR

(71) Applicant: Vital Connect, Inc., San Jose, CA (US)

(72) Inventors: Alexander Chan, Campbell, CA (US); Ravi Narasimhan, Campbell, CA (US); Nandakumar Selvaraj, Campbell, CA (US); Toai Doan, Campbell, CA (US)

(73) Assignee: Vital Connect, Inc., San Jose, CA (US)

( * ) Notice: Subject to any disclaimer, the term of this patent is extended or adjusted under 35 U.S.C. 154(b) by 0 days.

(21) Appl. No.: 15/985,896

(22) Filed: May 22, 2018

(65) Prior Publication Data

US 2018/0310879 A1    Nov. 1, 2018

Related U.S. Application Data

(63) Continuation of application No. 15/096,146, filed on Apr. 11, 2016, now Pat. No. 9,980,678, which is a (Continued)

(51) Int. Cl.
*A61B 5/00* (2006.01)
*A61B 5/0205* (2006.01)
(Continued)

(52) U.S. Cl.
CPC .......... *A61B 5/4884* (2013.01); *A61B 5/0006* (2013.01); *A61B 5/02055* (2013.01);
(Continued)

(58) Field of Classification Search
None
See application file for complete search history.

(56) References Cited

U.S. PATENT DOCUMENTS 7,160,253 B2    1/2007    Nissila
7,213,600 B2    5/2007    El-Nokaly et al.
(Continued)

FOREIGN PATENT DOCUMENTS

WO    2009138923 A1    11/2009

OTHER PUBLICATIONS

International Search Report and Written Opinion from International Application No. PCT/US2013/058302, dated Dec. 19, 2013.

*Primary Examiner* — Ankit D Tejani
(74) *Attorney, Agent, or Firm* — Brundidge & Stanger, P.C.

(57) ABSTRACT

A method and system for determining psychological acute stress are disclosed. In a first aspect, the method comprises detecting a physiological signal using a wireless sensor device, determining a stress feature using a normalized heart rate and a plurality of heart rate variability (HRV) features, wherein the normalized heart rate and the plurality of heart rate variability features are calculated using the detected physiological signal, and determining a stress level using the stress feature to determine the psychological acute stress. In a second aspect, the system comprises a wireless sensor device that includes a processor and a memory device coupled to the processor, wherein the memory device stores an application which, when executed by the processor, causes the wireless sensor device to carry out the steps of the method.

16 Claims, 8 Drawing Sheets

Related U.S. Application Data continuation-in-part of application No. 13/664,199, filed on Oct. 30, 2012, now Pat. No. 9,307,908.

(51) Int. Cl.

| | | |
|---|---|---|
| *A61B 5/11* | (2006.01) | |
| *A61B 5/0456* | (2006.01) | |
| *A61B 5/16* | (2006.01) | |
| *A61B 5/08* | (2006.01) | |
| *A61B 5/024* | (2006.01) | |
| *A61B 5/0468* | (2006.01) | |
| *A61B 5/021* | (2006.01) | |
| *A61B 5/0245* | (2006.01) | |

(52) U.S. Cl.
CPC ........ *A61B 5/02405* (2013.01); *A61B 5/0456* (2013.01); *A61B 5/0468* (2013.01); *A61B 5/08* (2013.01); *A61B 5/1117* (2013.01); *A61B 5/1118* (2013.01); *A61B 5/165* (2013.01); *A61B 5/7235* (2013.01); *A61B 5/021* (2013.01); *A61B 5/0245* (2013.01); *A61B 5/02116* (2013.01); *A61B 5/02416* (2013.01); *A61B 5/1116* (2013.01); *A61B 5/1123* (2013.01)

(56) References Cited

U.S. PATENT DOCUMENTS

| | | |
|---|---|---|
| 7,991,458 B2 | 8/2011 | Hardahl et al. |
| 9,307,908 B2 | 4/2016 | Chan et al. |
| 2006/0217615 A1 | 9/2006 | Huiku |
| 2008/0167565 A1 | 7/2008 | Laitio et al. |
| 2009/0292194 A1 | 11/2009 | Libbus et al. |
| 2009/0299159 A1* | 12/2009 | Scheiner ............ A61B 5/029 600/301 |
| 2011/0061647 A1 | 3/2011 | Stahmann |
| 2011/0270049 A1 | 11/2011 | Katra et al. |
| 2012/0022844 A1 | 1/2012 | Teixeira |
| 2012/0136226 A1 | 5/2012 | Wilke |
| 2014/0121543 A1 | 5/2014 | Chan et al. |

* cited by examiner

PSYCHOLOGICAL ACUTE STRESS MEASUREMENT USING A WIRELESS SENSOR

CROSS-REFERENCE TO RELATED APPLICATION

This application is a continuation of U.S. patent application Ser. No. 15/096,146, filed Apr. 11, 2016, which is a continuation-in-part of U.S. patent application Ser. No. 13/664,199, filed Oct. 30, 2012, now U.S. Pat. No. 9,307,908 both of which are incorporated herein by reference in their entirety.

FIELD OF THE INVENTION

The present invention relates to wireless sensor devices, and more particularly, to a wireless sensor device utilized to measure psychological acute stress.

BACKGROUND

Psychological stress is associated with a variety of major chronic health disorders and cardiovascular diseases and quantitatively measuring stress aids in stress management, which is essential to maintaining a low stress level. Conventionally, there are two types of psychological stress: acute stress and chronic stress. Acute stress is characterized by rapid changes in the autonomic nervous system that ready the body for "fight or flight" responses to external stimuli. Chronic stress is characterized by prolonged exposure to stressful stimuli which leads to long-term sympathetic over-activity.

Conventional methods of measuring stress calculate heart rate (HR) and heart rate variability (HRV) in the time and frequency domains. However, HR, HRV are highly variable between people. This variability limits the continuous monitoring and accurate measuring of a person's psychological stress levels. Therefore, there is a strong need for a cost-effective solution that overcomes the above issue by adaptively measuring individualized physiology. The present invention addresses such a need.

SUMMARY OF THE INVENTION

A method and system for determining psychological acute stress are disclosed. In a first aspect, the method comprises detecting a physiological signal using a wireless sensor device, determining a stress feature using a normalized heart rate and a plurality of heart rate variability (HRV) features, wherein the normalized heart rate and the plurality of heart rate variability features are calculated using the detected physiological signal, and determining a stress level using the stress feature to determine the psychological acute stress.

In a second aspect, the system comprises a wireless sensor device that includes a processor and a memory device coupled to the processor, wherein the memory device stores an application which, when executed by the processor, causes the wireless sensor device to detect a physiological signal using a wireless sensor device, determine a stress feature using a normalized heart rate and a plurality of heart rate variability (HRV) features, wherein the normalized heart rate and the plurality of heart rate variability features are calculated using the detected physiological signal, and determine a stress level using the stress feature to determine the psychological acute stress.

BRIEF DESCRIPTION OF THE DRAWINGS

The accompanying figures illustrate several embodiments of the invention and, together with the description, serve to explain the principles of the invention. One of ordinary skill in the art will recognize that the particular embodiments illustrated in the figures are merely exemplary, and are not intended to limit the scope of the present invention.

DETAILED DESCRIPTION OF PREFERRED EMBODIMENTS

Figure 1:
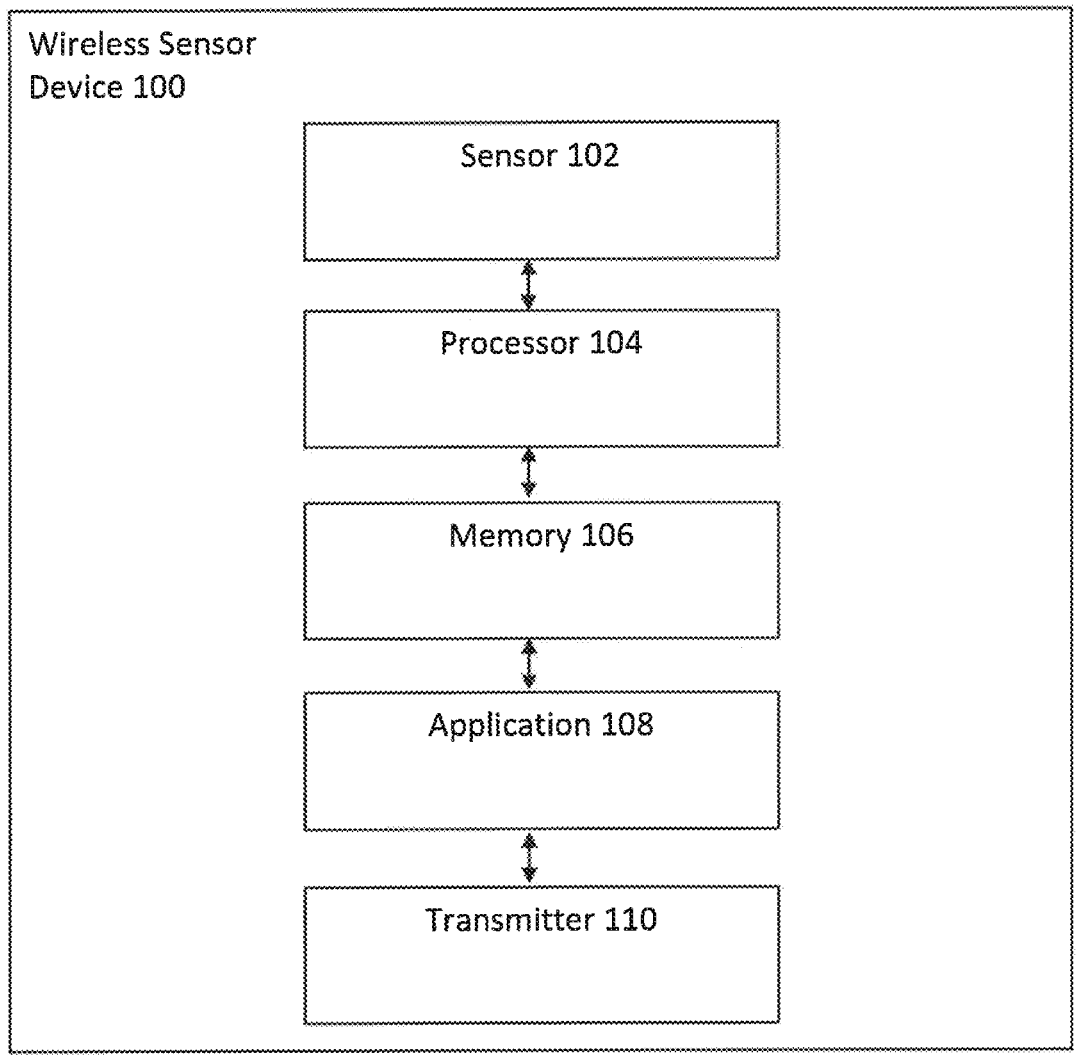
FIG. 1 illustrates a wireless sensor device for measuring psychological stress in accordance with an embodiment.

The present invention relates to wireless sensor devices, and more particularly, to a wireless sensor device utilized to measure psychological acute stress. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

The human body regulates its internal environment by various physiological processes, and maintains at a certain state of equilibrium called homeostasis. Stress is referred to as the disruption of homeostasis leading to a perturbed state of the human body. Stress can be triggered by various factors known as stressors including physical (e.g. diseases/illness, allergy, fatigue, and poor sleep), psychological (e.g. conflicts, trauma, financial state, and work/educational demands), and environmental (e.g. noise, crowd, disasters, and pollution) influences. The human body's reaction to the stressors is called a stress response, which is predominantly regulated by hypothalamic-pituitary-adrenocortical (HPA) and sympathetic-adrenal-medullary (SAM) systems. These systems interact by releasing stress hormones (glucocorticoids and catecholamines), and cause physiological changes related to vasomotor tones, heart rate variability (HRV), blood pressure, and sweat production at the body peripherals.

Stress is helpful in managing the demands at work/school, accomplishing goals/tasks, and generating fight-or-flight responses during times of danger. On the other hand, stress is one of the primary causes leading to major chronic health disorders including diabetes, obesity, heart disease, gastrointestinal conditions, depression, and anxiety problems.

Therefore, stress management is essential in this modern civilization to maintain one's stress level low, and reduce health risks. Stress levels are generally assessed based on self-assessment using questionnaires (e.g., State-Trait Anxiety Inventory (STAI)) and the perceived stress scale. Self-assessment is highly impractical for continual assessment, and it is also less reliable due to bias, random responding, and social compulsion to falsify the questionnaire responses to project a positive self-image.

Salivary-based noninvasive measurements such as salivary alpha-amylase (sAA) and salivary cortisol (sC) can be used to objectively quantify the psychosocial stress response in individuals. The sensitivity and reliability of salivary measurements are limited due to a number of factors including the sample volume, type of cotton rolls/swabs, and methodological issues such as time of sampling, assay conditions, storage, and compliance to the protocol. In addition, sC measurements can vary widely with body composition, age, gender, medication/nicotine use, and genetic factors. Stress can also be objectively detected using the physiological changes in blood pressure, HR, HRV, galvanic skin responses, and pupil diameter.

When left untreated, acute and chronic stress leads to a variety of health related challenges. Acute stress results in a "fight or flight" response to external stimuli. This response creates a short term increase in sympathetic tone and a decrease in parasympathetic tone. Acute stress is also characterized by an increased HR, increased low frequency HRV, decreased high frequency HRV, and a decreased galvanic skin response (GSR). Chronic stress results in long-term sympathetic overactivity. Chronic stress is also characterized by an increased baseline cortisol production, increased sympathetic activation, increased blood pressure, potentially decreased HRV, potential changes in HR, decreased physiological response to acute stress, and decreased baroreflex sensitivity.

HRV is related to the regulation of the heart by the autonomic nervous system. HRV is measured by a variety of time domain functions including but not limited to standard deviation of R-R intervals (SDNN), root-mean-square of successive R-R intervals (RMSSD), and a proportion of successive R-R intervals differing by a predetermined time period (e.g. >50 ms). An R-R interval is the interval from the peak of one QRS complex to the peak of the next as shown on an electrocardiogram. HRV is measured by a variety of frequency domain functions including but not limited to low frequency (LF) power from a predetermined range (e.g. 0.04 to 0.15 Hz), high frequency (HF) power from a predetermined range (e.g. 0.15 to 0.4 Hz), and a LF/HF ratio.

The person's psychological stress is measured by determining R-R intervals from an electrocardiogram (ECG) to calculate HRV features or metrics including but not limited to standard deviation of the R-R intervals (SDNN) and instantaneous heart rate (HR), wherein a stress feature (SF) is determined using the HRV metrics including SDNN and HR. After a predetermined time interval, adaptation is performed to update a probability mass function (PMF) of the stress feature (SF) and a stress level (SL) is determined using the SF and the PMF to continuously measure the psychological stress. The SL determination normalizes stress measurements between a value range of 0 to 1 because individual stress features (SFs) are highly variable.

Wearable smart sensors can capture the physiological and behavioral data in our day-to-day lives to correlate with stress. However, there are limited clinical-grade physiological monitors (wireless sensor devices) that can accurately quantify stress levels across a variety of individuals. A method and system in accordance with the present invention quantifies the psychological acute stress using a disposable adhesive biosensor (e.g. wireless sensor device, HealthPatch®, VitalPatch) worn on the chest of the user by using a stress index (SI) metric. The wireless sensor device tracks day-to-day patterns in HR, HRV, and SI levels which is useful in many clinical applications including but not limited to post-traumatic stress disorder, depression, and insomnia. The wireless sensor device in accordance with the present invention is a clinically validated disposable medical device worn on the user's chest that remotely monitors single lead ECG, HR, HRV, breathing rate, skin temperature, step counts, posture, fall detection, and continuously monitors changes in acute psychological stress levels.

Furthermore, the method and system in accordance with the present invention utilizes a combination of heart rate (HR) and heart rate variability metrics such as the SDNN and specific posture analysis to continuously measure stress levels of an individual person. Changing postures from sitting to standing and then from standing to walking increases a person's HR and decreases the HRV.

One of ordinary skill in the art readily recognizes that a variety of sensor devices can be utilized for the measuring of psychological stress including the HealthPatch® wearable and wireless sensor device, and other portable wireless sensor devices that include embedded circuitry and sensors in a disposable patch form factor and that would be within the spirit and scope of the present invention.

In one embodiment, the wireless sensor device utilized by the present invention to measure psychological acute stress is a disposable adhesive patch biosensor that incorporates two surface electrodes with hydrogel at the bottom side. An electronic module that consists of an embedded processor, tri-axial accelerometer, and Bluetooth Low energy (BLE) transceiver is inserted into the wireless sensor device and paired with a relay device (e.g. smartphone) for wireless data collection.

In this embodiment, the wireless sensor device is adhered to the chest and collects at least ECG measurements and tri-axial accelerations of the upper torso. The raw waveforms captured by the wireless sensor device is processed by embedded firmware algorithms on the electronic module thereby generating a plurality of physiological measurements including but not limited to HR, HRV, breathing rates, activity levels, energy expenditures, and psychological stress levels (via the stress index (SI) metric). The changes in psychological stress levels in individuals is detected based upon the changes in HR and HRV measurements at the constraint of no activity, and mapped to SI as a stress score (range of 0-100%).

To describe the features of the present invention in more detail, refer now to the following description in conjunction with the accompanying Figures.

FIG. 1 illustrates a wireless sensor device 100 for measuring psychological stress in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. The sensor 102 obtains physiological data from the user and transmits the data to the memory 106 and in turn to the application 108. The processor 104 executes the application 108 to process the physiological data of the user. The processed data is transmitted to the transmitter 110 and in turn relayed to another user or device.

In one embodiment, the sensor 102 comprises two electrodes to measure physiological and cardiac activity and an accelerometer to record physical activity and posture and the processor 104 comprises a microprocessor. One of ordinary skill in the art readily recognizes that a variety of devices can be utilized for any of the processor 104, the memory 106, the application 108, and the transmitter 110, and that would be within the spirit and scope of the present invention.

Figure 2:
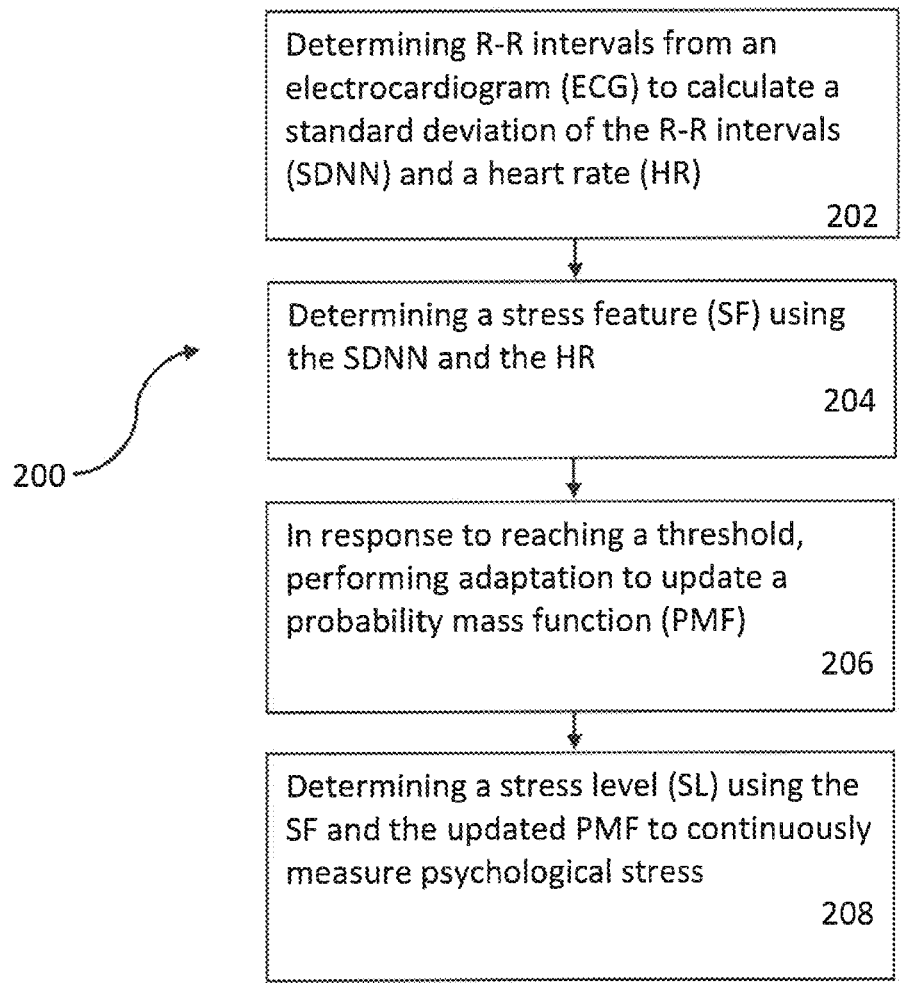
FIG. 2 illustrates a method for measuring psychological stress in accordance with an embodiment.

FIG. 2 illustrates a method 200 for measuring psychological stress in accordance with an embodiment. Referring to FIGS. 1 and 2 together, the method 200 comprises the wireless sensor device 100 determining R-R intervals from an electrocardiogram (ECG) to calculate a standard deviation of the R-R intervals (SDNN) and a heart rate (HR), via step 202, and determining a stress feature (SF) using the SDNN and the HR, via step 204. In response to reaching a threshold, the method 200 includes performing adaptation to update a probability mass function (PMF), via step 206. The method 200 includes determining a stress level (SL) using the SF and the PMF to continuously measure the psychological stress, via step 208.

In one embodiment, the method 200 further includes determining a posture state, wherein the psychological stress is not measured if the posture state is active. The posture state comprises a variety of states including but not limited to active (e.g. walking, running, etc.), siting, and standing. A separate probability mass function (PMF) is stored for each possible posture. In another embodiment, the method 200 further includes displaying the determined SL to a user or another device.

In one embodiment, determining R-R intervals from the ECG to calculate the SDNN and the HR via step 202 comprises coupling the wireless sensor device 100 via at least one electrode to measure the ECG of a user and detecting R peaks from the ECG within a predetermined time period. In this embodiment, the R-R intervals are calculated using the detected R peaks.

In one embodiment, determining a stress feature (SF) using the SDNN and the HR via step 204 comprises calculating a mean heart rate (HR) from the ECG within the predetermined time period and computing the SF utilizing an algorithm that includes the HR and the SDNN. In an embodiment, the algorithm is SF=HR+$\alpha$*SDNN, wherein a is predetermined negative variable that allows for combining HR and SDNN.

In another embodiment, if the wireless sensor device 100 records other relevant physiologic parameters, for example, galvanic skin response (GSR), skin temperature (TEMP), breathing rate (BR), and a square root of the mean squared difference of successive NNs (RMSSD) is utilized to compute HRV, the algorithm to compute SF is a linear combination of the parameters, for example, SF=$\alpha 1$*HR+$\alpha 2$*SDNN+$\alpha 3$*RMSSD+$\alpha 4$*GSR+$\alpha 5$*TEMP+$\alpha 6$*BR. In another embodiment, the SF is a non-linear combination of these measures, for example, the algorithm is SF=$HR^2$+$\alpha 1$*sqrt(SDNN)+$\alpha 2$*RMSSD*GSR or SF=$\alpha 1$*HR+$\alpha 2$*log(SDNN)+$\alpha 3$*$TEMP^2$+$\alpha 4$*exp(-GSR).

In one embodiment, performing adaptation to update the PMF via step 206 comprises grouping data into a predetermined distribution, calibrating the predetermined distribution according to a detected resting heart rate, and adjusting the predetermined distribution according to additional samples received. In an embodiment, adjusting the predetermined distribution according to additional samples received comprises multiplying all bins of the predetermined distribution by 1-$\varepsilon$ in response to data arriving and adding $\varepsilon$ to a bin corresponding to the data.

In one embodiment, determining the stress level (SL) using the SF and the PMF via step 208 comprises adding all bins below a bin corresponding to the SF, and computing the SL utilizing an algorithm that includes a probability mass function for a given posture ($PMF_{posture}$), the SF, and the added bins. In this embodiment, the method 200 further includes adding a fraction of a current bin of the SL to improve granularity.

Long-term (e.g. weeks, months) changes in the mean and standard deviation of a stress feature probability mass function (PMF) reflects increases and/or decreases in stress. In one embodiment, the method 200 further includes tracking both a mean and a standard deviation of a probability mass function (PMF) as the PMF adapts over time and combining the mean and standard deviation to measure long-term stress.

Figure 3:
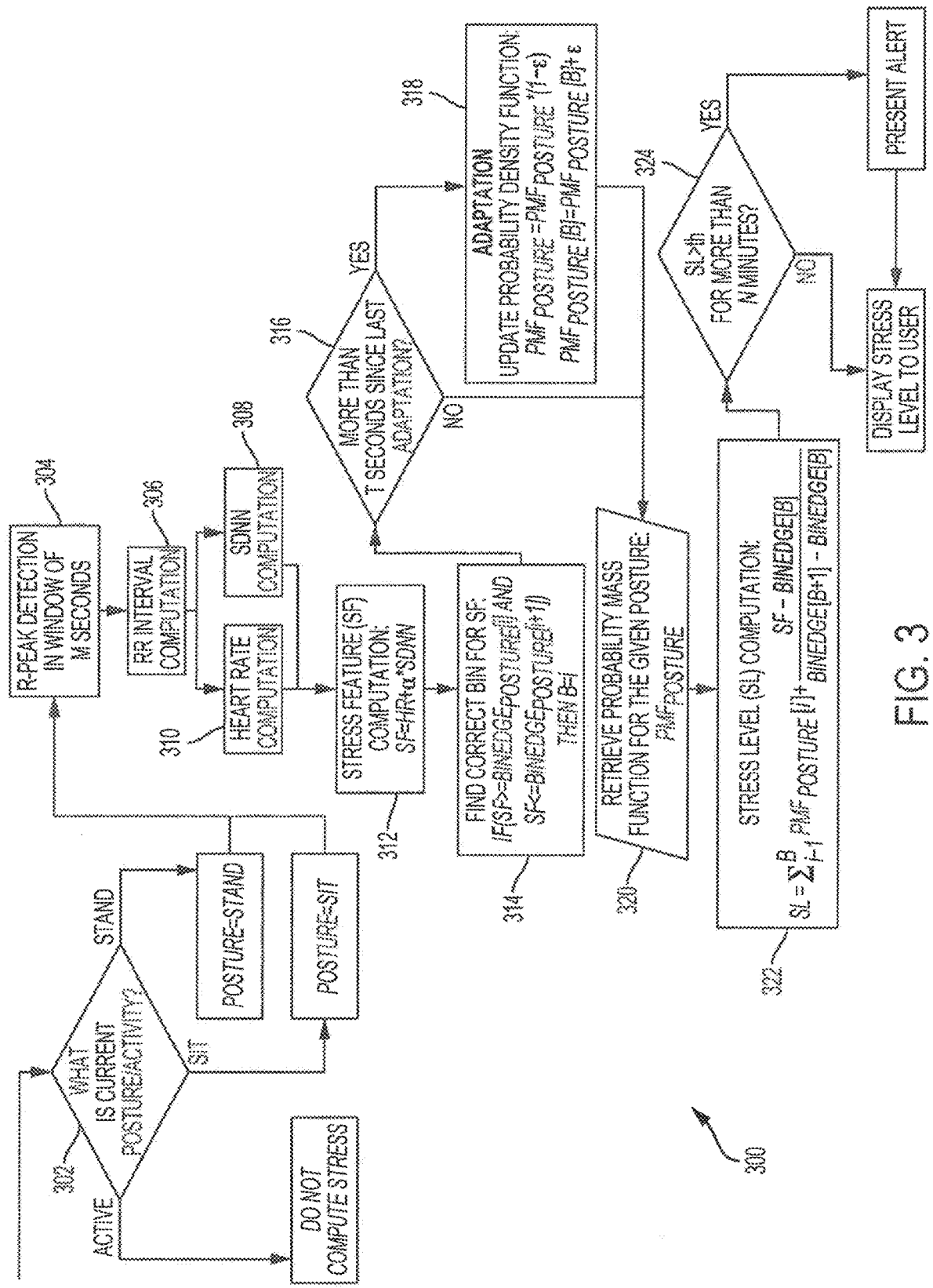
FIG. 3 illustrates a more detailed flow chart of a method for measuring psychological stress in accordance with an embodiment.

FIG. 3 illustrates a more detailed flow chart of a method 300 for measuring psychological stress in accordance with an embodiment. The method 300 includes determining the current posture/activity of a user, via step 302. If the posture/activity is "active", the method 300 does not compute a stress level. If the posture/activity is either "stand" or "sit", the method 300 computes a stress level. The method 300 detects R-peaks within a predetermined time period, via step 304, computes R-R intervals, via step 306, computes a standard deviation of R-R intervals (SDNN), via step 308, and computes a heart rate (HR), via step 310.

Utilizing these computations, the method 300 computes a stress feature (SF) per the following equation: SF=HR+$\alpha$*SDNN, via step 312. The SF is highly variable between individuals and in one embodiment, is between a predetermined range of -20 to 160. Because of this variability, a standardized stress level with a value range between 0 and 1 is computed that is relatively normalized between people. The a value is typically negative and is the weighting that allows for combining HR and SDNN and in one embodiment, a is defaulted as -0.315. The method 300 includes finding a correct bin for the SF per the following equation: IF (SF>=$binedge_{posture}$[i] AND SF<$binedge_{posture}$[i+1]), THEN B=i, via step 314.

The $binedge_{posture}$[i] includes the edges of the bins for the stress feature and the number of bins and spacing of bin edges is set depending upon desired granularity. In one embodiment, for 180 bins from -20 to 160, bin edges are set as -20, -19, -18 . . . , 159, 160). The bins are used for the PMF/histogram and B is the bin that the current SF falls into.

The method 300 determines whether more than a predetermined number of seconds (T) has passed since a last adaptation, via step 316. In one embodiment, T is defaulted as 600 seconds. If yes (more than T seconds have passed since the last adaptation), then the method 300 updates a probability mass function (PMF) via an adaptation function per the following equation: $PMF_{posture}$=$PMF_{posture}$*(1-$\varepsilon$) and $PMF_{posture}$[B]=$PMF_{posture}$[B]+$\varepsilon$, where $\varepsilon$ is a "forgetting" parameter for how much the PMF/histogram is changed with each adaptation run, via step 318. In one embodiment, $\varepsilon$ is defaulted as 0.0003. The method 300 retrieves a probability mass function (PMF) for the given posture as $PMF_{posture}$, via step 320, which is used to calculate the stress level (SL).

The stress level (SL) measures the stress of an individual on a scale from 0 to 1, where 0 indicates no or very little stress and 1 indicates extremely high stress. The method 300 computes the SL per the following equation, via step 322:

$$SL = \sum_{i=1}^{B} PMF_{posture}[i] + \frac{SF - binedge[B]}{binedge[B+1] - binedge[B]}.$$

In this equation, all the bins below the current bin B that the SF falls into are added and a fraction of the current bin B is added to result in improved granularity. There is a separate probability mass function (PMF) for each posture because different postures have different HR and SDNN values. The method 300 determines whether the computed SL is greater than a threshold (th) for more than N minutes, via step 324. If yes, an alert is presented to the user. After the SL is computed, it is displayed via the wireless sensor device 100.

In one embodiment, the adaptive function comprises initializing, calibrating, and adapting steps. The initializing step includes beginning with a group probability mass function (PMF) that is a discretized Gaussian distribution predetermined from group training data. The calibrating step includes shifting the probability distribution according to detected resting heart rates. The adapting step includes adjusting the PMF as new samples arrive or as frequently/infrequently as desired. When new data arrives, all bins are multiplied by 1-$\varepsilon$ (e.g. 0.9997) and c (e.g. 0.0003) is added to a bin corresponding to the new data. This adaptation adjusts the probability distribution over the course of days to weeks to fit the particular person's average distribution of stress over the course of the day.

Figure 4:
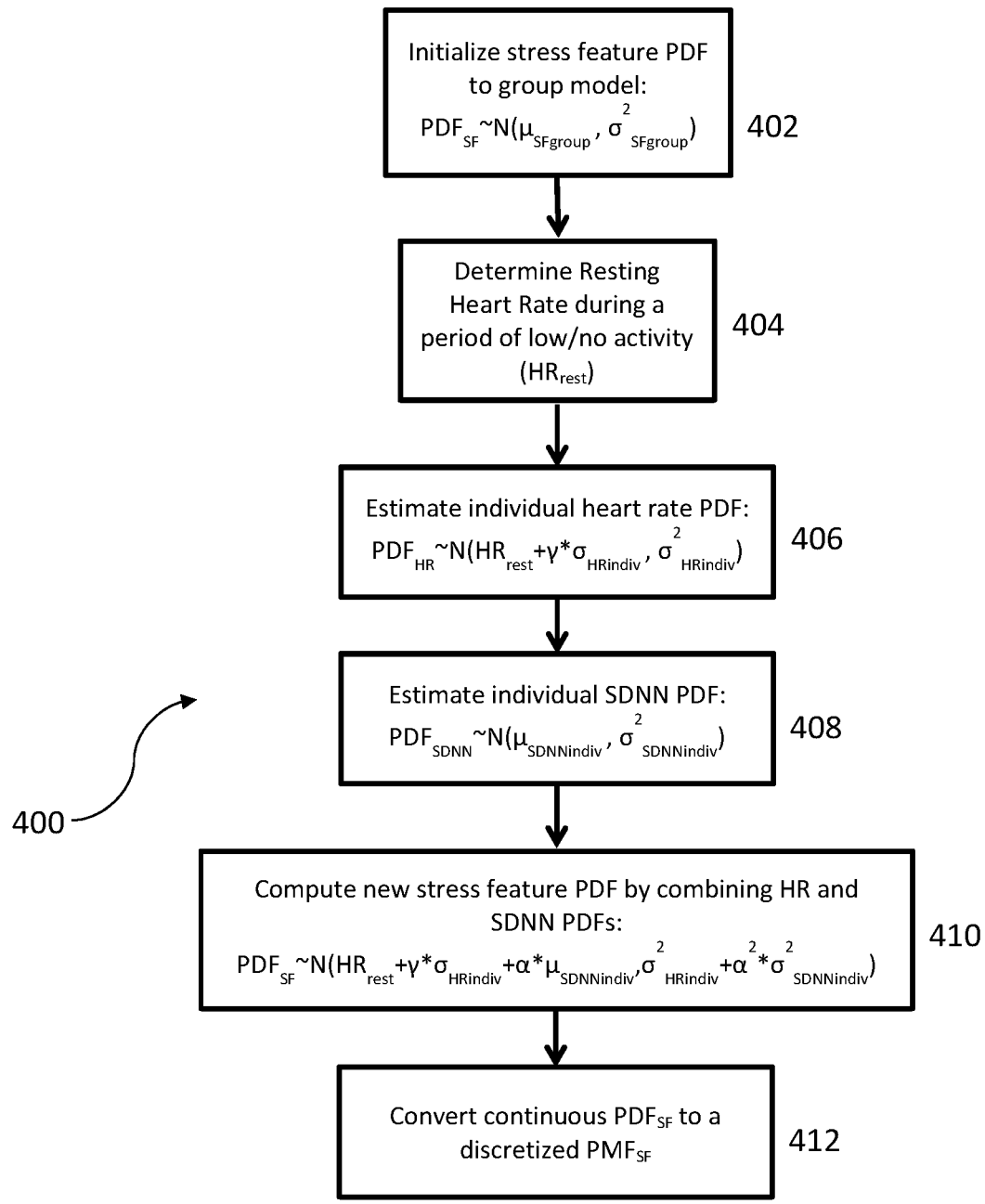
FIG. 4 illustrates a more detailed flow chart of a method for adaptive function calibration in accordance with an embodiment.

FIG. 4 illustrates a more detailed flow chart of a method 400 for adaptive function calibration in accordance with an embodiment. The method 400 includes initializing a stress feature probability density function (PDF) to a predetermined group model per the following equation: $PDF_{SF} \sim N(\mu_{SFgroup}, \sigma^2_{SFgroup})$, via step 402. The notation $N(\mu, \sigma^2)$ is a normal/Gaussian distribution with mean $\mu$ and variance $\sigma^2$ and $\mu_{SFgroup}$ and $\sigma^2_{SFgroup}$ are predetermined from the group training data.

The method 400 determines a resting heart rate ($HR_{rest}$) of a user during a period of low or no activity, via step 404. The $HR_{rest}$ is estimated from the user's data and can be during no activity or sleep periods. The method 400 estimates an individual heart rate (HR) PDF per the following equation: $PDF_{HR} \sim N(HR_{rest}+\gamma^*\sigma_{HRindiv}, \sigma^2_{HRindiv})$, via step 406 and estimates an individual SDNN PDF per the following equation: $PDF_{SDNN} \sim N(\mu_{SDNNindiv}, \sigma^2_{SDNNindiv})$, via step 408. The method 400 computes a new stress feature PDF by combining the determined HR and SDNN PDFs per the following equation: $PDF_{SF} \sim N(HR_{rest}+\gamma^*\sigma_{HRindiv}+\alpha^*\mu_{SDNNindiv}, \alpha^2\sigma^2_{HRindiv}+\alpha^2*\sigma^2_{SDNNindiv})$, via step 410. The continuous $PDF_{SF}$ is converted to a discretized probability distribution, or probability mass function ($PMF_{SF}$), via step 412. In one embodiment, the conversion is done by sampling the $PDF_{SF}$ within a predetermined interval and normalizing the sum to 1.

In one embodiment, the $\gamma$ value is a constant offset above $HR_{rest}$ for the mean of the HR distribution (e.g. $\gamma=2$). The $\sigma_{HRindiv}$, $\sigma_{SDNNindiv}$, $\mu_{SDNNindiv}$ values are predetermined and fixed and are computed from the group training data. The $\sigma_{HRindiv}$ and $\sigma_{SDNNindiv}$ values are computed as the mean of the individual standard deviations in the group training data and the $\mu_{SDNNindiv}$ value is computed as the mean of the mean SDNN of all individuals in the group training data.

Long-term changes in the mean and standard deviation of the stress feature PMF reflect increases or decreases in stress. Increased chronic stress is seen in an upwards long-term shift of the SF probability distribution and increased chronic stress also decreases the response to acute stress, resulting in a narrow SF probability distribution or a smaller standard deviation.

In one embodiment, tracking the mean and the standard deviation of this SF probability distribution as it adapts over time and combining these results enables a measure of long-term stress per the following equation: $SF_{long}=\mu_{SF}-\beta^*\sigma_{SF}$, where $\mu_{SF}$ is the mean of the SF from the current probability distribution $$\left(\mu_{SF} = \sum_i SF_i * PMF[SF_i]\right),$$

$\sigma_{SF}$ is the standard deviation of the SF from the current probability distribution $$\left(\sigma^2_{SF} = \sum_i |SF_i - \mu_{SF}|^2 * PMF[SF_i]\right),$$

and B is a positive value.

If a person's mean stress feature probability mass function/probability distribution ($PMF_{SF}$) increases over time, $\mu_{SF}$ will increase and $SF_{long}$ will increase. If a person becomes less responsive to acute stress due to chronic stress, the standard deviation of the SF distribution will decrease because they are not responding to different increases/decreases in acute stress, resulting in the $\sigma_{SF}$ decreasing and the $SF_{long}$ once again increasing. In one embodiment, $SF_{long}$ is computed from the current $PMF_{SF}$ at various time periods including but not limited to once every few days and tracked over various time periods including but not limited to weeks and months.

In one embodiment, to determine the group training data, users are subjected to alternating blocks of relaxation and stress. The blocks ranged from 3 to 7 minutes in length, relaxation involved various acts including but not limited to sitting quietly or listening to classical music, and stress involved various acts including but not limited to watching a movie clip from an active/horror movie, playing tetris, performing a stroop test, performing a series of mental arithmetic problems, and playing a competitive online real-time strategy game.

Figure 5:
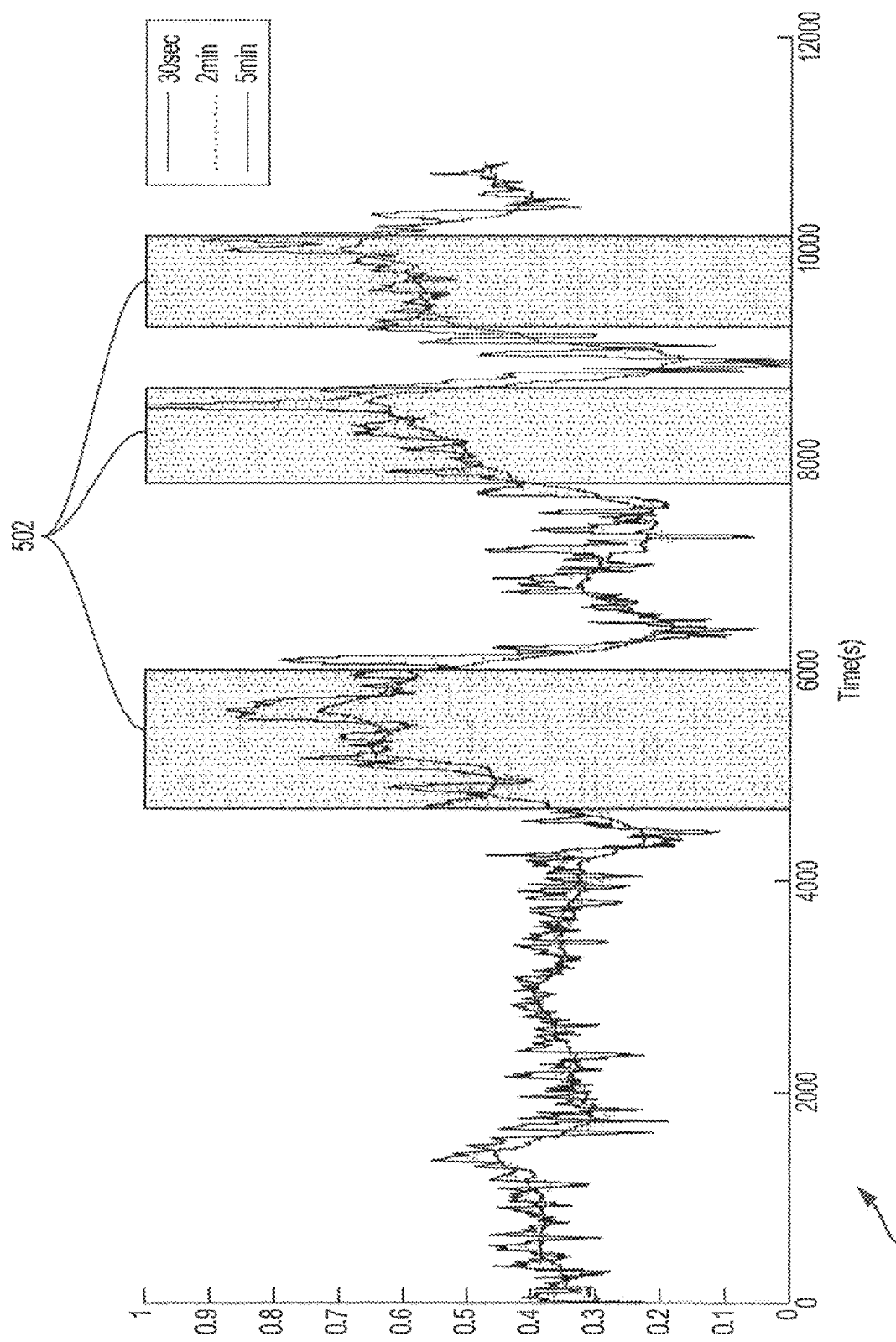
FIG. 5 illustrates a diagram of stress level calculation in accordance with an embodiment.

FIG. 5 illustrates a diagram 500 of stress level calculation in accordance with an embodiment. In the diagram 500, the y axis represents the stress level from 0 to 1 and the x axis represents time. A predetermined window of time for computing the stress level is variable depending on the necessary time resolution and the application (e.g. gaming versus daily use). Shorter windows allow changes in stress to be detected much faster but include additional noise. During periods of stress 502, such as playing a game, the stress level increases to values closer to 1.

Additionally, while the probability mass function (PMF) is adapted for each person, the best stress feature or the best combination of HR and SDNN is learnable for each person. In one embodiment, individual learning is done via supervised learning including but not limited to Fisher Discriminants that learn the best a, which is the weighting parameter for combining HR and SDNN for each person.

In an embodiment, a semi-supervised approached is utilized to learn the best feature including but not limited to self-training where an individual performs a few minutes of a relaxation activity (e.g. metronome breathing) and a few minutes of a stressful activity (e.g. playing tetris). The two data points are used to determine an initial projection line defined by the a parameter and new data is classified and the most confident data points are used by the wireless sensor device 100 to continuously and automatically adjust the a parameter.

Figure 6:
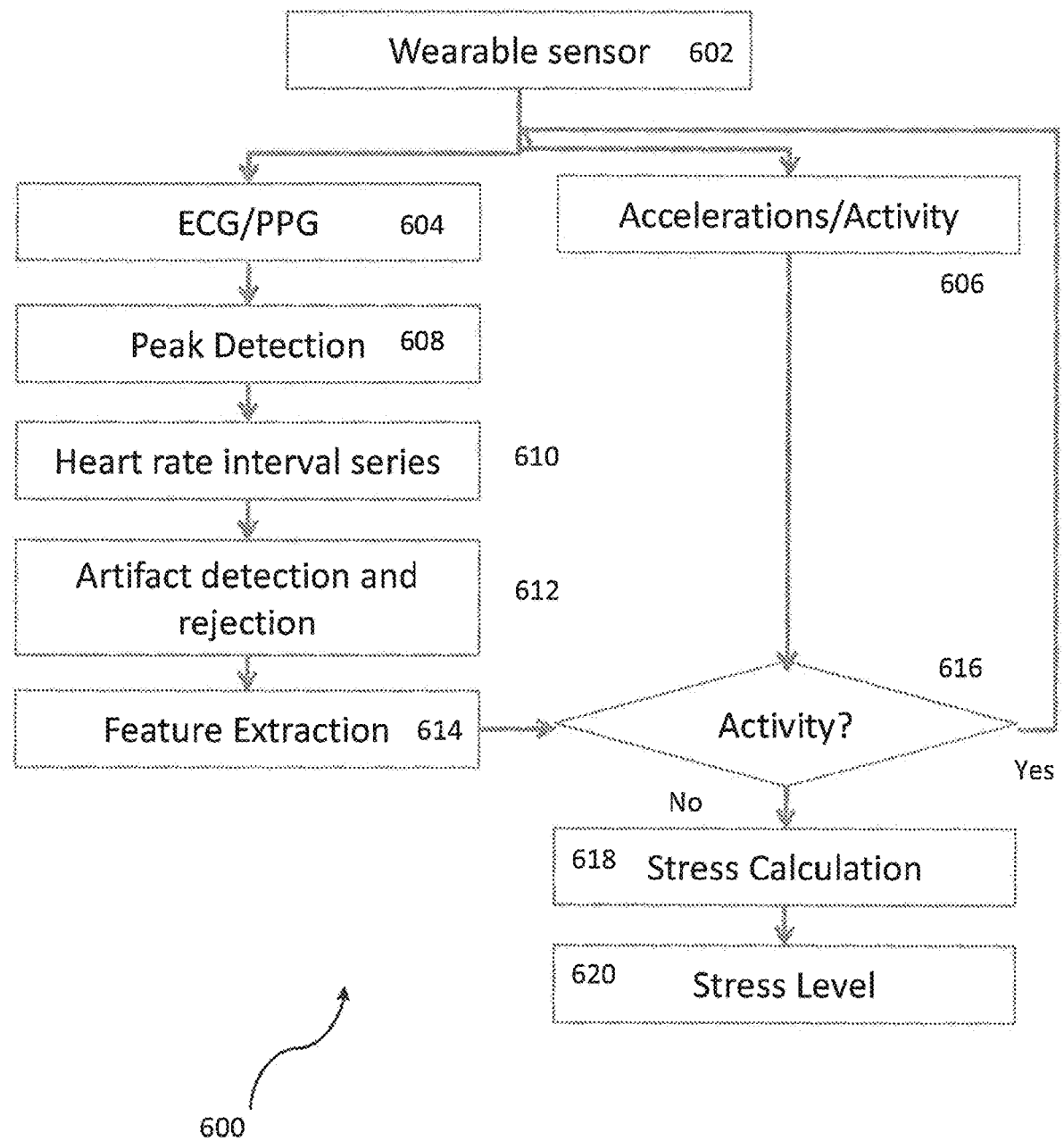
FIG. 6 illustrates a method for determining psychological acute stress using a stress index (SI) metric in accordance with an embodiment.

FIG. 6 illustrates a method 600 for determining psychological acute stress using a stress index (SI) metric in accordance with an embodiment. The method 600 provides a wearable sensor (wireless sensor device) attached to a user in locations including the chest, wrist, or ear, via step 602, to detect electrocardiogram (ECG)/photoplethysmogram (PPG) signals (raw waveforms), via step 604, and to detect accelerations and activity levels, via step 606. During the peak detection process, via step 608, the wireless sensor device detects R peaks of the ECG signal or systolic peaks of the PPG signal.

The wireless sensor device utilizes the detected successive peaks to calculate heart rate interval series, via step 610, by determining the time intervals (HR intervals) between successive R peaks or systolic peaks. The wireless sensor device then detects and rejects artifact beat values (noise) from the heart rate interval series to provide pruned beat-to-beat heart rate interval values, via step 612, and the pruned beat-to-beat heart rate interval values are used to extract a plurality of HRV features, via step 614. The feature extraction process, via step 614, of the plurality of features is further described below in FIG. 7.

The method 600 further comprises the wireless sensor device determining whether there has been any activity by the user, via step 616. In one embodiment, the wireless sensor device detects acceleration signal and activity levels of the user using embedded sensors such as an accelerometer. The wireless sensor device can utilize a predetermined threshold level for the activity level to determine whether there has been any activity.

If yes (the user has been active or active at or above the predetermined threshold level), the method 600 returns back to step 602 and the cardiovascular and activity metrics are detected again by the wireless sensor device via steps 604 and 606. If no (the user has not been active or very minimal activity levels that are at or below the predetermined threshold level have been detected), the method 600 continues and the wireless sensor device utilizes the feature extraction output garnered from step 614 to provide a stress calculation, via step 618.

The stress calculation involves the previously described steps of 312-322 of FIG. 3 where the stress feature (SF) is calculated using the linear or nonlinear combination of the plurality of HRV features, the probability mass function (PMF) is retrieved for a given posture, and the stress level (SL) is calculated using both the SF and the PMF. The stress level calculation of step 618 is given on a scale between 0 and 1 or 0-100%, via step 620.

Figure 7:
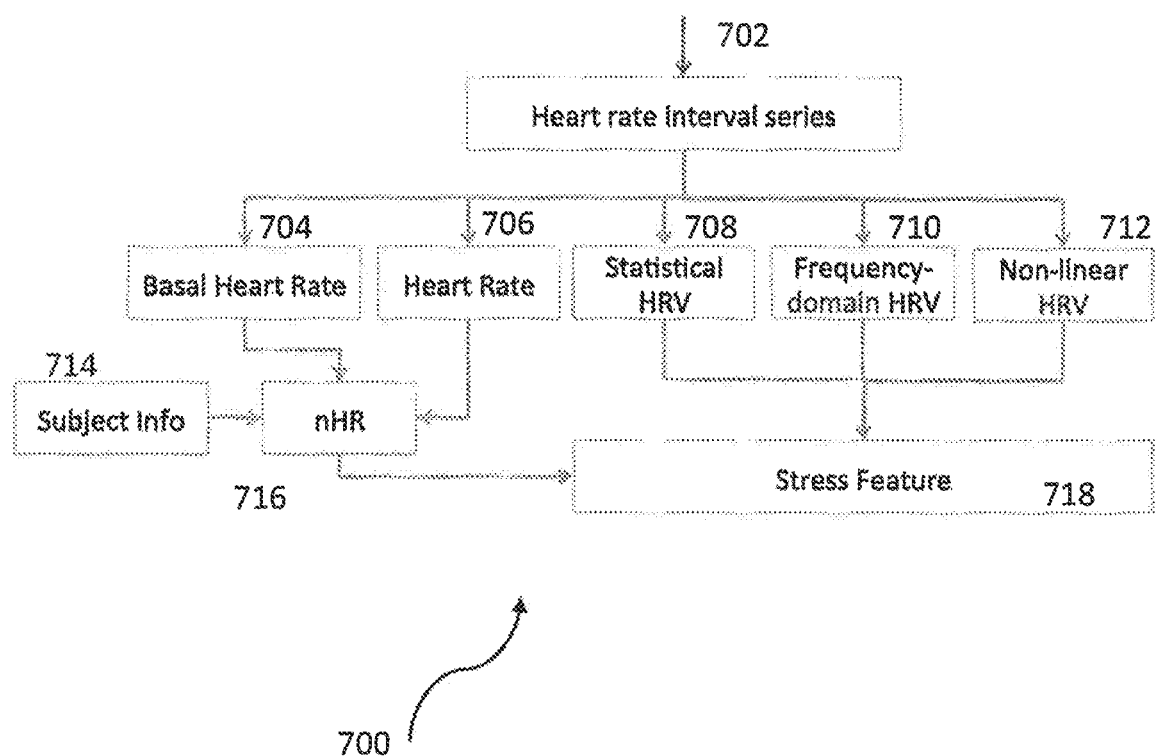
FIG. 7 illustrates a method for feature extraction in accordance with an embodiment.

FIG. 7 illustrates a method 700 for feature extraction in accordance with an embodiment. The method 700 provides additional details regarding the feature extraction step of 614 from FIG. 6. Referring to FIG. 6 and FIG. 7 together, the pruned beat-to-beat heart rate interval values (output from step 612 of FIG. 6) is represented by step 702 which is first process step in method 700. The pruned heart rate interval values are used to determine a continuous basal heart rate ($HR_b$), via step 704. The continuous basal heart rate is a low-pass filtered signal of the pruned heart rate interval values (instantaneous heart rate interval values) with a constraint of inactivity that tracks a very low frequency trend in heart rate during rest conditions. The pruned heart rate interval values over a number of beats (e.g., 124 beats) or a moving time window (e.g., 2 min) are used by the wireless sensor device to calculate the average heart rate, via step 706, a statistical HRV, via step 708, a frequency-domain HRV, via step 710, and a non-linear HRV, via step 712.

In one embodiment, the instantaneous heart rate values are calculated as the ratio of 60 over the pruned heart rate interval values in seconds. The statistical HRV features, determined via step 708, include but are not limited to the standard deviation of HR intervals (SDNN) and the root mean square successive differences of the HR intervals (RMSSD). The frequency-domain HRV features, determined via step 710, include but are not limited to the absolute or normalized spectral band powers including low-frequency band (0.04-0.15 Hz) and high frequency band (0.15-0.4 Hz) and the ratio of spectral band powers (LF/HF ratio). The non-linear HRV features, determined via step 712, include but are not limited to the approximate entropy that measures complexity or regularity of the HR time interval series data and Poincare plot measures including short-term HRV (SD1) and long-term HRV (SD2).

The method 700 obtains subject information from the user, via step 714, and combines the continuous basal heart rate and the average heart rate measurements from steps 704 and 706 to determine a normalized heart rate (nHR), via step 716. In one embodiment, the subject information includes a plurality of information including but not limited to age. In one embodiment, the nHR is calculated by the wireless sensor device as the heart rate reserve (HRR) according to the following equation: $HRR=(HR-HR_b)/(HR_{max}-HR_b)$, where $HR_{max}=208-0.7*Age$ or $HR_{max}=220-Age$.

In other embodiments, the nHR is calculated as either $HR/HR_b$ or $HR-HR_b$. The normalization of the heart rate allows scaling the stress level (SL) uniformly across a plurality of individuals with different backgrounds (age, gender, etc) and health (athletes, smokers, diabetics, etc). Since the HR values vary widely across individuals in normal conditions, the change in HR from their baseline due to psychological stress can result in changes in stress level restricted to a particular region (low, mid, high level on a scale of 0 to 1 or 0 to 100%). For example, the wireless sensor device may determine that individuals with a low baseline HR values have a low stress level despite detecting an increase in HR from their low baseline due to psychological stress.

On the other hand, the wireless sensor device may determine that individuals with a high baseline HR values have a high stress level even though they are not stressed out. The normalized heart rate (nHR) calculated via step 716 and the plurality of HRV features (statistical via step 708, frequency-domain via step 710, non-linear via step 712) are combined to determine a stress feature value, via step 718. The stress feature value is either a linear or a nonlinear model as a function of the plurality of HRV features. Accordingly, the stress feature value (SF) is calculated as a weighted sum of features similar to step 312 of FIG. 3, the stress level (SL) is calculated using the stress feature value (SF) similar to step 322 of FIG. 3, and the stress index (SI) metric is the stress level (SL) given in a percentage (%) scale.

Figure 8:
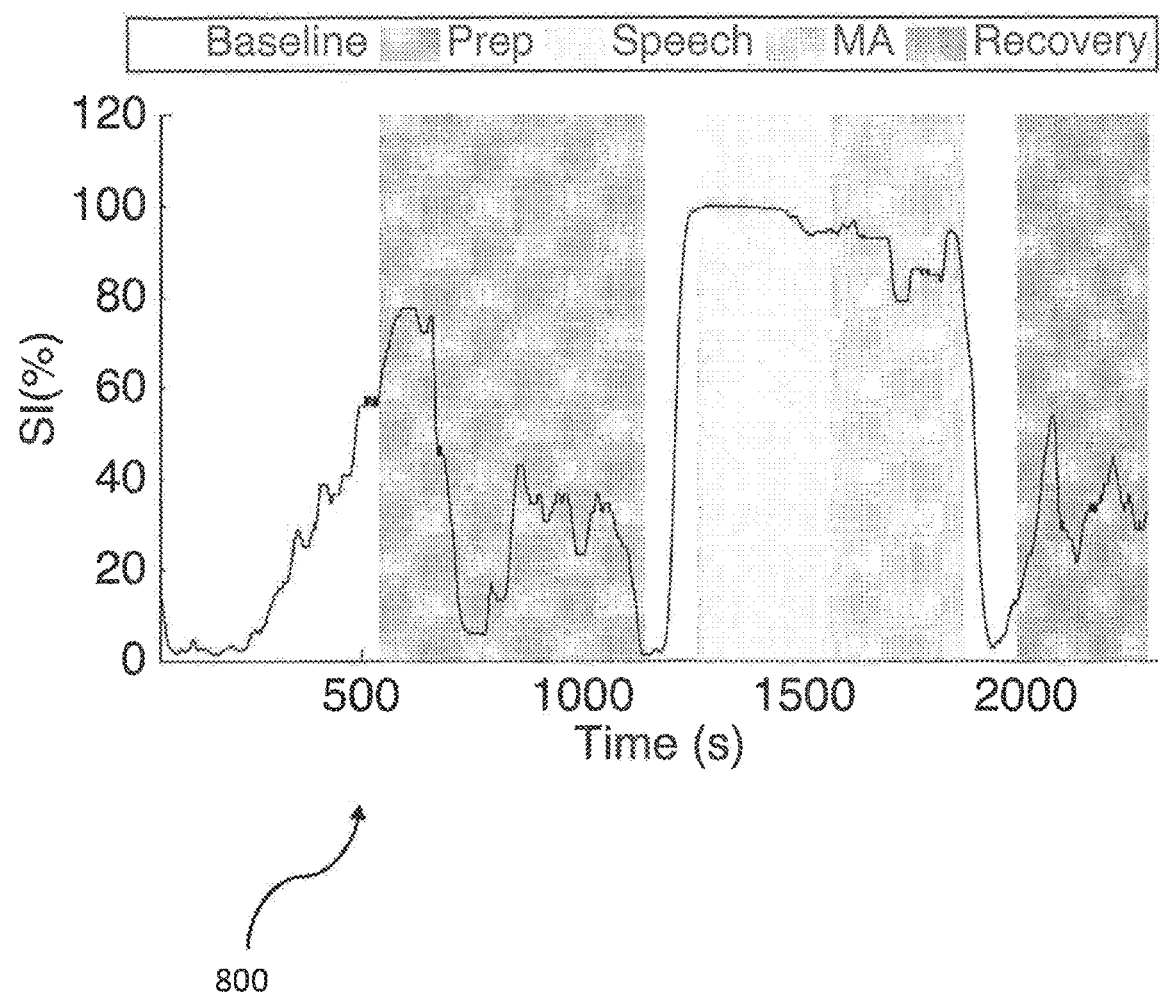
FIG. 8 illustrates a diagram of stress index (SI) metric calculation in accordance with an embodiment.

FIG. 8 illustrates a diagram 800 of stress index (SI) metric calculation in accordance with an embodiment. The stress index (SI) metric is the stress level given in %. In diagram 800, the wireless sensor device accurately calculates an increase in the stress index (SI) metric to approximately 100% levels during when the user conducted the stressful speech and the mental arithmetic (MA) tasks. The stress index (SI) metric started at a 0% level, gradually increased as the preparation started, peaked during the stressful activities, and dropped back down to the recovery period as denoted in diagram 800.

In one study, healthy subjects were attached with one HealthPatch® wireless sensor device at the left pectoralis major muscle along the cardiac axis to record modified Lead-II ECG. The subjects carried out a standard Trier Social Stress Test (TSST) protocol. During the study, the subjects filled out state anxiety form-Y1 of the State Anxiety Inventory questionnaire (sSTAI). Salivary samples were obtained from the subjects for salivary alpha-amylase (sAA) and salivary cortisol (sC) measurements and the HealthPatch® sensor data was wireless acquired.

The data analyses revealed that sSTAI scores were significantly increases (P<0.001) due to TSST compared to the baseline. However, the changes in both sAA and sC measurements were not significant (P=0.281 and P=0.792, respectively). On the other hand, the SI metric data from the HealthPatch® sensor showed a significant (P<0.001) increase (50%) during TSST, and was shown to be sensitive to objectively tracking acute changes in psychological stress. Therefore, the HealthPatch® biosensor can continuously monitor the psychological health of users leading to the effective management of stress and a healthier life.

In one embodiment, a method and system for determining psychological acute stress of a user of a wireless sensor device are disclosed. The method comprises detecting a physiological signal using the wireless sensor device, determining a stress feature using a normalized heart rate and a plurality of heart rate variability (HRV) features, wherein the normalized heart rate and the plurality of HRV features are calculated using the detected physiological signal, and determining a stress level using the stress feature to determine the psychological acute stress.

The plurality of HRV features include statistical HRV features, frequency-domain HRV features, and non-linear HRV features. The statistical HRV features include but are not limited to any of a standard deviation of HR intervals (SDNN) and a root mean square successive differences of HR intervals (RMSSD), the frequency-domain HRV features include but are not limited to any of absolute or normalized spectral band powers and a ratio of spectral band powers (LF/HF ratio), and the non-linear HRV features include any of an approximate entropy measuring complexity of HR time interval series data of the physiological signal and Poincare plot measures.

In one embodiment, the method further comprises determining whether an activity level threshold is reached (e.g., a low activity level to ensure stress level calculations are only carried out when the user is not active) and wherein if the activity level threshold is reached, detecting another physiological signal prior to the determining of the stress feature.

In one embodiment, the plurality of HRV features are calculated by performing peak detection on the physiological signal to provide a plurality of successive peaks, calculating a heart rate interval series using the plurality of successive peaks, removing artifacts from the heart rate interval series to provide beat-to-beat pruned heart rate interval values, and extracting features from the pruned beat-to-beat plurality of HRV features to provide the plurality of HRV features.

In one embodiment, the physiological signal is any of an electrocardioagram (ECG) signal and a photoplethysmogram (PPG) signal. The peak detection detects R peaks of the ECG signal or systolic peaks of the PPG signal. In one embodiment, the extracting of the features from the pruned beat-to-beat plurality of HRV features step further comprises determining a continuous basal heart rate using the pruned beat-to-beat plurality of HRV features, determining an average heart rate using the pruned beat-to-beat plurality of HRV features, and a calculation of the continuous basal heart rate over a predetermined time period, and determining the plurality of HRV features using a calculation of the continuous basal heart rate over a predetermined time period (e.g., a number of beats such as 124 beats or a moving time window such as 2 minutes).

In one embodiment, the calculation of the normalized heart rate (nHR) is carried out utilizing a combination of the continuous basal heart rate and the average heart rate using the following equation: $HRR=(HR-HR_b)/(HR_{max}-HR_b)$, where $HR_b$ is the continuous basal heart rate, HR is the average heart rate, and $HR_{max}=(208-0.7*Age)$ or (220-Age). The determining of the stress level step further comprises determining a probability mass function (PMF) for a detected posture, calculating the stress level using both the stress feature and the probability mass function, and providing the stress level as a stress index (SI) metric on a predetermined scale (e.g., 0 to 1 or 0 to 100%).

In one embodiment, the system comprises a wireless sensor device (e.g., HealthPatch®) for determining the psychological acute stress. The wireless sensor device includes a processor and a memory device coupled to the processor, wherein the memory device stores an application which, when executed by the processor, causes the wireless sensor device to carry out the aforementioned steps of the method.

As above described, the method and system allow for measuring psychological acute stress of a user using a wireless sensor device. By determining current posture, detecting R-peaks from an ECG or systolic peaks from a PPG within a predetermined window of time to calculate a plurality of HRV features or metrics, combining the plurality of HRV metrics with a normalized heart rate to calculate a stress feature (SF) that is highly variable between different people, determining a current bin that the SF falls into within a predetermined bin range, determining a latest probability mass function (PMF), and summing all bins of the PMF below the current bin, a cost-effective and continuous stress level (SL) measurement system is achieved.

The predetermined window of time includes but is not limited to 120 seconds and the predetermined bin range includes but is not limited to −20 to 160 with a width of 1. If a threshold time period has passed since last adaptation, the method and system perform adaptation of the probability mass function (PMF)/probability distribution using the current SF. The current stress level (SL) of the user is either displayed to the user via the wireless sensor device and/or triggers a warning alert if the SL is above a threshold (th) longer than a predetermined time period of N minutes.

In addition, the wireless sensor device utilizes the vital/physiological measurements of HR and HRV to determine a normalized HR and a stress feature vector and then calculates the stress index (SI) metric to provide feedback about the patient's stress levels, offer awareness about his/her state of mind, and help prevent and detect cardiac and stress related diseases. The wireless sensor device is thus valuable for the continuous monitoring of psychological health and the effective management of stress leading to a healthy life regardless of user individuality.

A method and system for determining psychological acute stress has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable storage medium providing program code or program instructions for use by or in connection with a computer or any instruction execution system. For the purposes of this description, a computer-usable or computer-readable storage medium can be any apparatus that can contain, store, communicate, propagate, or transport the program for use by or in connection with the instruction execution system, apparatus, or device.

The computer-readable storage medium may be an electronic, magnetic, optical, electromagnetic, infrared, semiconductor system (or apparatus or device), or a propagation medium. Examples of a computer-readable storage medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for determining psychological acute stress by a wireless sensor device, the method comprising:
   detecting a physiological signal;
   detecting accelerations and determining a posture state from the detected accelerations;
   storing a separate probability mass function (PMF) for each of a plurality of postures;
   calculating a normalized heart rate using the detected physiological signal;
   calculating a plurality of heart rate variability (HRV) features using the detected physiological signal;
   determining whether an activity level threshold is reached based on the detected accelerations and posture state;
   in response to the activity level threshold being reached, detecting another physiological signal prior to a determination of a stress feature; and in response to the activity level threshold not being reached,
      determining the stress feature using the normalized heart rate and the plurality of heart rate variability (HRV) features,
      determining a stress level using the stress feature and PMF to determine the psychological acute stress, and
      displaying the determined stress level via the wireless sensor device.

2. The method of claim 1, further comprising performing peak detection on the physiological signal to provide a plurality of successive peaks.

3. The method of claim 2, wherein the peak detection detects R peaks of the ECG signal or systolic peaks of the PPG signal.

4. The method of claim 2, further comprising calculating heart rate intervals by determining time intervals between successive R peaks or systolic peaks.

5. The method of claim 4, further comprising removing artifacts from series of the heart rate intervals to provide pruned heart rate interval values.

6. The method of claim 5, further comprising extracting features from the pruned plurality of HRV features to provide the plurality of HRV features.

7. The method of claim 6, wherein the extracting step further comprises:
   determining a continuous basal heart rate using the pruned heart rate interval values;
   determining an average heart rate using the pruned heart rate interval values; and
   determining the plurality of HRV features using a calculation of the pruned heart rate interval values over a predetermined time period.

8. The method of claim 1, wherein the posture state includes a physical activity level.

9. A wireless sensor device for determining psychological acute stress, the wireless sensor device including a processor and a memory device coupled to the processor, wherein the memory device stores an application which, when executed by the processor, causes the wireless sensor device to:
   detect a physiological signal;
   detect accelerations and determine a posture state from the detected accelerations;
   store a separate probability mass function (PMF) for each of a plurality of postures;
   calculate a normalized heart rate using the detected physiological signal;
   calculate a plurality of heart rate variability (HRV) features using the detected physiological signal;
   determine whether an activity level threshold is reached based on the detected accelerations and posture state;
   in response to the activity level threshold being reached, detecting another physiological signal prior to a determination of a stress feature; and
   in response to the activity level threshold not being reached,
      determine the stress feature using the normalized heart rate and the plurality of heart rate variability (HRV) features,
      determine a stress level using the stress feature and PMF to determine the psychological acute stress, and
      display the determined stress level via the wireless sensor device.

10. The wireless sensor device of claim 9, wherein the memory device stores the application which, when further executed by the processor, causes the wireless sensor device to perform peak detection on the physiological signal to provide a plurality of successive peaks.

11. The wireless sensor device of claim 10, wherein the peak detection detects R peaks of the ECG signal or systolic peaks of the PPG signal.

12. The wireless sensor device of claim 10, wherein the memory device stores the application which, when further executed by the processor, causes the wireless sensor device to calculate heart rate intervals by determining time intervals between successive R peaks or systolic peaks.

13. The wireless sensor device of claim 12, wherein the memory device stores the application which, when further executed by the processor, causes the wireless sensor device to remove artifacts from series of the heart rate intervals to provide pruned heart rate interval values.

14. The wireless sensor device of claim 13, wherein the memory device stores the application which, when further executed by the processor, causes the wireless sensor device to extract features from the pruned plurality of HRV features to provide the plurality of HRV features.

15. The wireless sensor device of claim 14, wherein the extraction step further comprises:
  determine a continuous basal heart rate using the pruned heart rate interval values;
  determine an average heart rate using the pruned heart rate interval values; and
  determine the plurality of HRV features using a calculation of the pruned heart rate interval values over a predetermined time period.

16. A non-transitory computer-readable medium storing executable instructions that, in response to execution, cause a computer to perform operations comprising:
  detecting a physiological signal;
  detecting accelerations and determining a posture state from the detected accelerations;
  storing a separate probability mass function (PMF) for each of a plurality of postures;
  calculating a normalized heart rate using the detected physiological signal;
  calculating a plurality of heart rate variability (HRV) features using the detected physiological signal;
  determining whether an activity level threshold is reached based on the detected accelerations and posture state;
  in response to the activity level threshold being reached, detecting another physiological signal prior to a determination of a stress feature; and
  in response to the activity level threshold not being reached,
    determining a stress feature using the normalized heart rate and the plurality of heart rate variability (HRV) features,
    determining a stress level using the stress feature and PMF to determine the psychological acute stress, and
    displaying the determined stress level via the wireless sensor device.

* * * * *